(12) United States Patent
Chodkowski et al.

(10) Patent No.: US 11,571,537 B2
(45) Date of Patent: Feb. 7, 2023

(54) ADHESIVE ALIGNMENT SYSTEM FOR PATIENT INTERFACES

(71) Applicant: KONINKLIJKE PHILIPS N.V., Eindhoven (NL)

(72) Inventors: Lauren Patricia Chodkowski, Pittsburgh, PA (US); Natasha A. Gilbert, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 402 days.

(21) Appl. No.: 16/822,454

(22) Filed: Mar. 18, 2020

(65) Prior Publication Data

US 2020/0306483 A1    Oct. 1, 2020

Related U.S. Application Data

(60) Provisional application No. 62/825,239, filed on Mar. 28, 2019.

(51) Int. Cl.
*A61M 16/06* (2006.01)
*B33Y 80/00* (2015.01)

(52) U.S. Cl.
CPC .... *A61M 16/0688* (2014.02); *A61M 16/0605* (2014.02); *A61M 2016/0661* (2013.01); *A61M 2207/10* (2013.01); *B33Y 80/00* (2014.12)

(58) Field of Classification Search
CPC ........... A61M 16/06–0694; A61M 2016/0661; A61M 2207/10; B33Y 80/00
See application file for complete search history.

(56) References Cited

U.S. PATENT DOCUMENTS

| 7,506,649 B2 | 3/2009 | Doshi et al. |
| 8,291,906 B2 | 10/2012 | Barlow et al. |
| 8,522,785 B2 | 9/2013 | Berthon-Jones et al. |
| 8,869,798 B2 | 10/2014 | Cariola et al. |
| 8,905,031 B2 | 12/2014 | Barlow |
| 9,220,860 B2 | 12/2015 | Davidson et al. |
| 2010/0101581 A1* | 4/2010 | Lang ...................... B29C 66/63 425/134 |
| 2013/0139822 A1* | 6/2013 | Gibson ............. A61M 16/0616 128/205.25 |

(Continued)

FOREIGN PATENT DOCUMENTS

WO    WO-2017108763 A1 *    6/2017    ............ A61M 16/06

OTHER PUBLICATIONS

International Search Report for PCT/EP2020/058842 dated Mar. 27, 2020.

*Primary Examiner* — Valerie L Woodward
(74) *Attorney, Agent, or Firm* — Michael W. Haas

(57) ABSTRACT

A system for aligning a patient interface for use in delivering a flow of a breathing gas to the airway of a patient with an adhesive arrangement that is structured to secure the patient interface to the patient. The system includes a base that is structured to be disposed on a surface, the base having a central member protruding upward from the base to a contoured surface. The central member includes a pair of protruding alignment elements that extend further upward from the contoured surface and which are sized and structured to engage apertures in both of the adhesive arrangement and the patient interface in a manner which aligns such components with each other.

14 Claims, 5 Drawing Sheets

(56) References Cited

U.S. PATENT DOCUMENTS

| | | |
|---|---|---|
| 2015/0352307 A1 | 12/2015 | Rutan |
| 2017/0049983 A1* | 2/2017 | Ellis .................. B29C 51/082 |
| 2018/0043122 A1* | 2/2018 | Oenning ........... A61M 16/0605 |
| 2020/0016358 A1* | 1/2020 | Bornholdt ............. A61M 16/16 |

* cited by examiner

ADHESIVE ALIGNMENT SYSTEM FOR PATIENT INTERFACES

CROSS-REFERENCE TO RELATED APPLICATIONS

This patent application claims the priority benefit under 35 U.S.C. § 119(e) of U.S. Provisional Application No. 62/825,239, filed on Mar. 28, 2019, the contents of which are herein incorporated by reference.

BACKGROUND OF THE INVENTION

1. Field of the Invention

The present invention relates to systems for aligning a patient interface, such as a nasal mask, with an adhesive arrangement used in securing the patient interface to the face of a patient. The present invention also relates to methods for aligning a patient interface with an adhesive arrangement for use in securing the patient interface to the patient.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion member on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the pressure support device with the airway of the patient, so that a flow of breathing gas can be delivered from the pressure/flow generating device to the airway of the patient.

Traditionally, such patient interface devices have been secured to the face/head of the patient by a headgear component having one or more straps which wrap around all, or a portion, of the patient's head. Recently, adhesive arrangements have been employed, either in-whole, or in-part, to secure patient interface devices to the face of a patient. In such arrangements, many concerns/complaints are related to the strength of the adhesive and the ease of removal of the adhesive. Another major concern/complaint is alignment of the adhesive arrangement used to secure the patient interface with the patient interface itself as misalignment of such elements will result in a low quality fitment which is uncomfortable to patient and may not provide proper treatment due to leaks.

SUMMARY OF THE INVENTION

Accordingly, as one aspect of the present invention a system for aligning a patient interface for use in delivering a flow of a breathing gas to the airway of a patient with an adhesive arrangement structured to secure the patient interface to the patient is provided. The system comprises a base structured to be disposed on a surface, the base comprising a central member protruding upward from the base to a contoured surface, the central member including a pair of protruding alignment elements extending further upward from the contoured surface.

The patient interface may be a nasal mask having a pair of nasal apertures, and each protruding alignment element may be sized and configured to cooperatively engage a corresponding nasal aperture of the patient interface device.

The nasal apertures may be defined within a contoured surface of the patient interface, and the contoured surface of the base may be of a shape which is structured to coincide with the contoured surface of the patient interface.

The system may further comprise a clamping arrangement moveably coupled to the base, the clamping arrangement being structured to hold the adhesive arrangement in a predetermined position on the base.

The base may comprise a first support surface structured to support a portion of the adhesive arrangement and a second support surface structured to support another portion of the adhesive arrangement; and the clamping member may comprise: a first clamping surface; and a second clamping surface, wherein the clamping arrangement is movable relative to the base between: a first positioning in which the first clamping surface is disengaged and spaced from the first support surface and the second clamping surface is disengaged and spaced from the second support surface, and a different second positioning in which the first clamping surface is engaged, directly or indirectly with the first support surface and the second clamping surface is engaged, directly or indirectly with the second support surface. The clamping arrangement may comprise a first arm member having a first end and an opposite second end and a second arm member having a first end and an opposite second end; wherein the first end of the first arm member is moveably coupled to the base; wherein the first end of the second arm member is moveably coupled to the base; wherein the first clamping surface is disposed at or about the second end of the first arm member; and wherein the second clamping surface is disposed at or about the second end of the second arm member. The first arm member may comprise a first portion of a unitary member moveably coupled to the base and the second arm member may comprise a second portion of the unitary member. The unitary member may be pivotally coupled to the base.

The base may be formed from an additive manufacturing process. The base may be dimensioned, at least in-part, based on dimensions obtained from the patient. The contoured surface of the base may be dimensioned based on facial dimensions of the patient. The first support surface, the second support surface, the first clamping surface, and the second clamping surface may be positioned and shaped based on facial dimensions of the patient.

The base may further comprise a custom indicia selected by the patient integrally formed therewith.

As another aspect of the present invention a method of aligning a patient interface for use in delivering a flow of a breathing gas to the airway of a patient with a primary adhesive arrangement structured to secure the patient interface to the patient using a system is provided. The system comprises: a base structured to be disposed on a surface, the base comprising a central member protruding upward from the base to a contoured surface, the central member including a pair of protruding alignment elements extending further upward from the contoured surface. The method comprises: positioning the primary adhesive arrangement on the base such that a pair of first apertures of the primary adhesive arrangement are positioned such that the pair of protruding alignment elements of the base extend through the pair of first apertures; positioning a secondary adhesive arrangement on the primary adhesive arrangement such that a pair of second apertures of the secondary adhesive arrangement are positioned such that the pair of protruding alignment elements of the base extend through the pair of second apertures; and positioning the patient interface on the secondary adhesive arrangement such that a pair of nasal apertures of the patient interface are positioned such that the pair of protruding alignment elements of the base extend through the pair of nasal apertures.

The base may further comprise a clamping arrangement moveably coupled to the base, the clamping arrangement being structured to hold the primary adhesive arrangement in a predetermined position on the base; and the method may further comprise securing the primary adhesive arrangement to the base with the clamping arrangement prior to positioning the secondary adhesive arrangement on the primary adhesive arrangement.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

Figure 1:
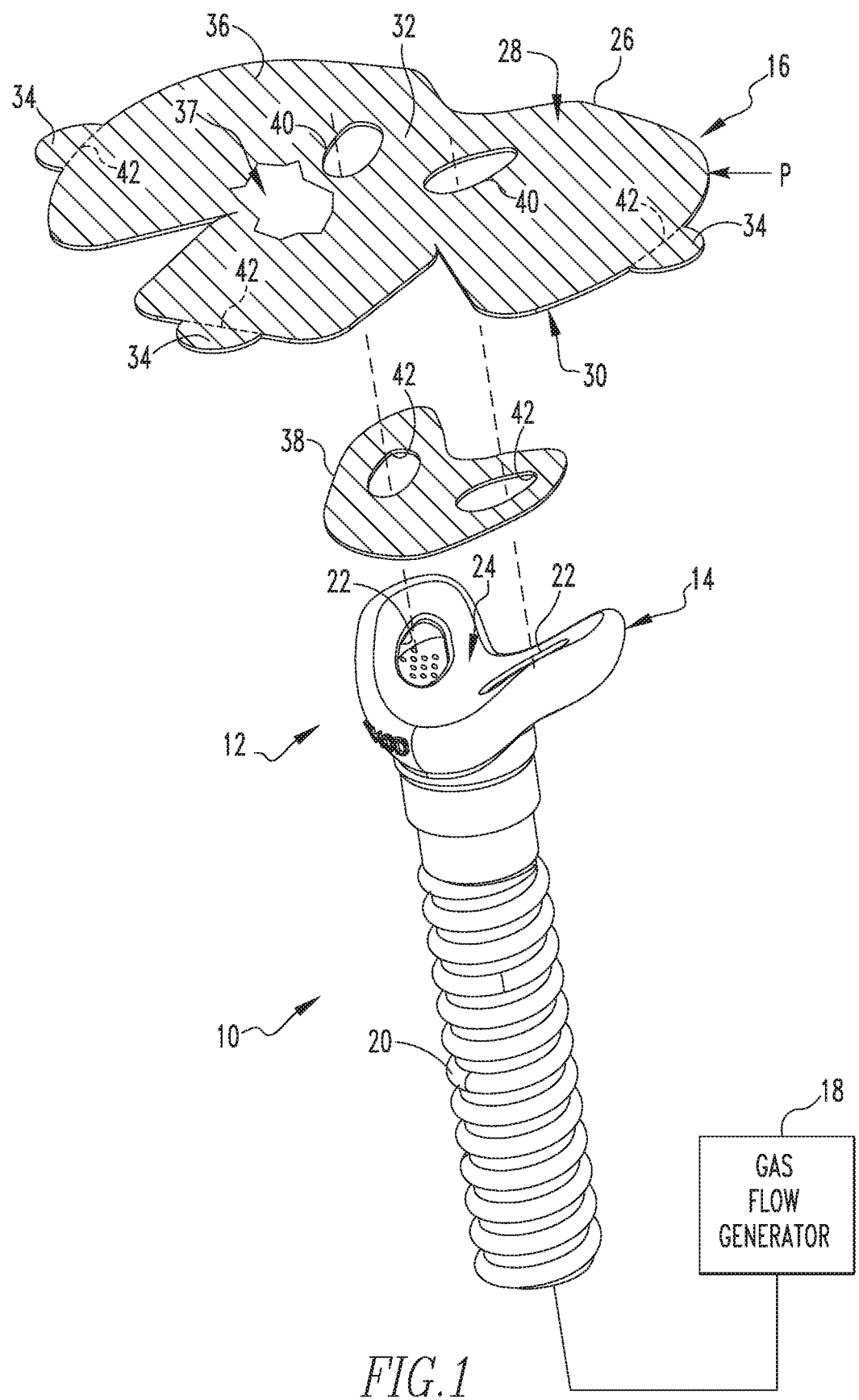
FIG. 1 is a simplified perspective front view of an airway pressure support system including a patient interface and adhesive arrangement which may be aligned utilizing a system in accordance with one non-limiting example embodiment of the present invention.

As required, detailed embodiments of the present invention are disclosed herein; however, it is to be understood that the disclosed example embodiments described herein are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are coupled directly in contact with each other. As used herein, "fixedly coupled" or "fixed" means that two components are coupled so as to move as one while maintaining a constant orientation relative to each other.

As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a simplified perspective front view of an airway pressure support system 10 including a patient interface assembly 12 having a patient interface 14 and an adhesive arrangement 16 for use in providing a flow of a breathing gas to the airway of a patient (not shown) which may be aligned utilizing an alignment system in accordance with one non-limiting example embodiment of the present invention. Airway pressure support system 10 includes a gas flow generator 18 (shown schematically) and a hose 20 (partially shown schematically) having a first end (not numbered) coupled to gas flow generator 18 and an opposite second end (not numbered) coupled to patient interface 14. Gas flow generator 18 is structured to generate a flow of breathing gas to be delivered to an airway of a patient via hose 20 and patient interface 14.

In the example arrangement shown in FIG. 1, patient interface 14 is in the form of a cradle-like nasal interface for generally engaging the underside of the nose of a patient. Accordingly, patient interface 14 includes a pair nasal apertures 22 defined in a contoured surface 24. In one example embodiment of the present invention, contoured surface 24 and each nasal aperture 22 is custom dimensioned/formed based on facial dimensions of a particular patient. Such custom dimensioning/forming may readily be carried out using 3D scanning and printing techniques known in the art. It is to be appreciated however, that other arrangements of patient interface 12 may be employed without varying from the scope of the present invention.

Continuing to refer to FIG. 1, adhesive arrangement 16 is provided for securing patient interface 14 to the face of a patient. Adhesive arrangement 16 is formed from a generally thin (e.g., having a thickness of at least 0.04 mm) substantially planar substrate material 26 having a first planar surface 28, which faces toward a patient, and a second planar surface 30, opposite first planar surface 28, which faces toward patient interface 14. Planar substrate material 26 may generally be any pliable material such as, for example, without limitation, foam, silicone polyurethane, latex, or any other suitable material. Planar substrate material 26 includes a main portion 32 having a number of tabs 34 projecting outward therefrom. Adhesive arrangement 16 further includes an adhesive material 36 (shown schematically as hatching, e.g., without limitation, a silicone or acrylic based adhesive layer or any other suitable adhesive layer) provided on first planar surface 28 for use in adhering adhesive arrangement 16 to the skin of a patient. In one embodiment, a layer of a release film 37 (only a portion of which is shown in FIG. 1) is provided covering adhesive material 36 for shielding adhesive material 36 until desired to be adhered to the skin of a patient.

After removing the aforementioned release film, and prior to adhering substrate material 26 to the skin of a patient, each tab 34 is folded back onto main portion 32 such that the adhesive material 36 on tab 34 is adhered to the adhesive material 36 on main portion 32, thus fixing each tab 34 in a positioning on first planar surface 28. As adhesive material 36 is only disposed on first planar surface 28 portion of each tab 34 and not on the second planar surface 30, such positioning of tabs 34 on first planar surface 28 effectively provides for a non-adhesive area extending from a periphery P of main portion 32 that is generally surrounded by adhesive material 36 by about 180 degrees, if not more. Such non-adhesive areas provide for an underlying area that can be readily engaged by a fingertip of a patient, and gripped via a thumb positioned on second planar surface 30 of main portion 32 opposite such non-adhesive area in order to peel away all, or selected portions of adhesive arrangement 16 from the skin of the patient.

In example system 10 illustrated in FIG. 1, adhesive arrangement 16 is structured to be positioned generally between patient interface 14 and the skin of the patient. More particularly, adhesive arrangement 16 is structured to be positioned between contoured surface 24 of patient interface 14 and the skin of the patient and secured to contoured surface 24 via a secondary adhesive arrangement 38 (e.g., a single layer material having upper and lower adhesive surfaces integral therewith or applied thereto) which may be disposed directly on second planar surface 30 of substrate material 26, or alternatively, as a separate element, such as shown in the example of FIG. 1. In order to provide for a reliable seal about each nare of the patient, and to allow for the passage of the flow of breathing gas from each of nasal apertures 22 of patient interface 14 to the respective nares of the patient, each of adhesive substrate material 26, and similarly secondary adhesive arrangement 38, respectively includes a pair of apertures 40 and 42 defined therein of similar, and preferably identical shape (e.g., to minimize turbulence, maximize comfort, etc.), as nasal apertures 22.

Referring now to FIGS. 2-5, a system 100 for readily and predictably aligning patient interface 14, adhesive arrangement 16, and secondary adhesive arrangement 38. System 100 includes a base 102 that is structured to be disposed on a surface (e.g., without limitation, a table, counter, nightstand, etc.) and a clamping arrangement 104 moveably coupled to base 102 that is structured to generally hold adhesive arrangement 16 in a predetermined position on base 102.

Base 102 includes a central member 106 protruding upward therefrom to a contoured surface 108 which, in one example embodiment of the present invention is of a shape which is structured to coincide with contoured surface 24 of patient interface 14. A pair of protruding alignment elements 110 extend further upward from contoured surface 108. In the one example embodiment shown in the figures, each protruding alignment element 110 is sized and configured so as to cooperatively engage a respective one of apertures 40 of adhesive arrangement 16, a respective one of one of apertures 42 of secondary adhesive arrangement 38, and a corresponding one of nasal apertures 22 of patient interface 14, as discussed further below in conjunction with FIGS. 7 and 8. Base 102 further includes a first support surface 112 structured to support a portion of adhesive arrangement 16 and a second support surface 114 structured to support another portion of adhesive arrangement 16.

Figure 7:
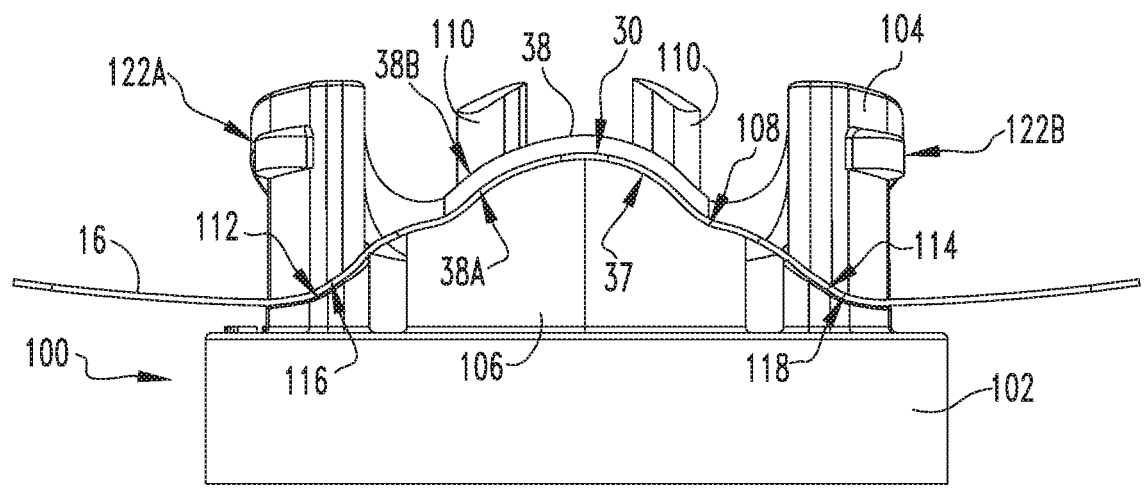
FIG. 7 is another front elevation view of the system of FIG. 2 similar to FIG. 3 but showing the adhesive arrangement of FIG. 1 positioned on a contoured surface of the system and generally clamped thereon by the clamping member which is disposed in a clamped position.
Figure 8:
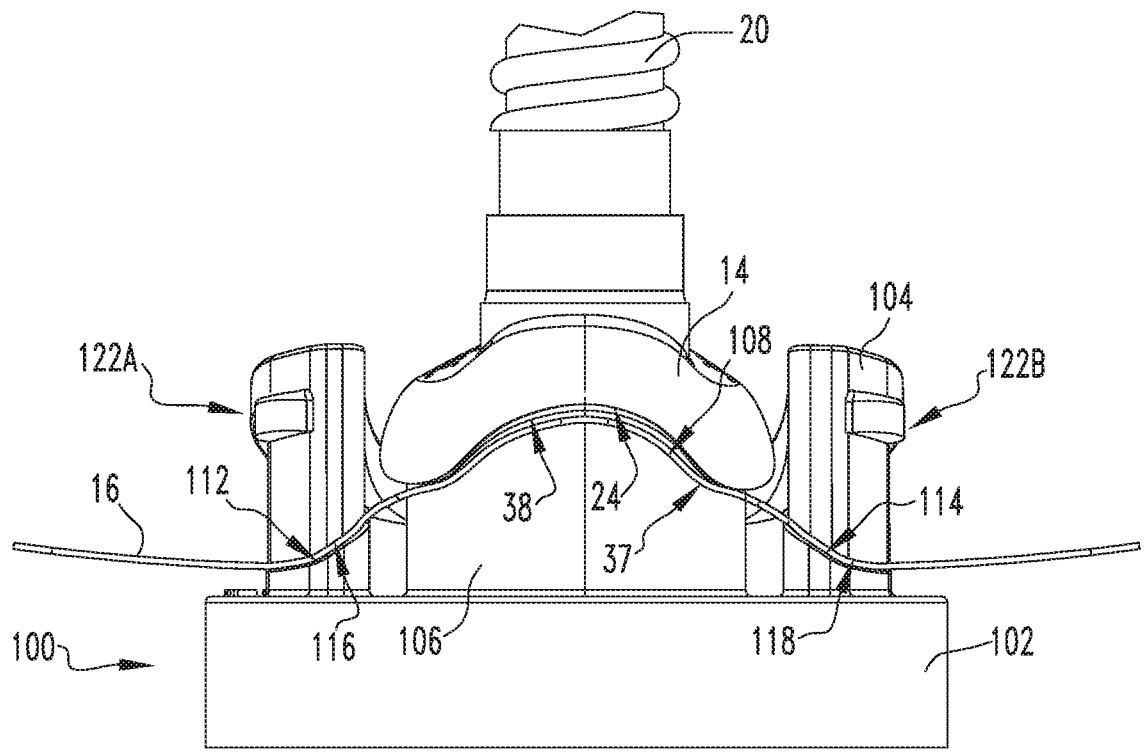
FIG. 8 is yet another front elevation view of the system of FIG. 2 similar to FIG. 7 but further including the patient interface of FIG. 1 engaged with alignment structures of the system and adhered to an adhesive portion of the adhesive arrangement.

Continuing to refer to FIGS. 2-5, clamping arrangement 104 includes a first clamping surface 116 and a second clamping surface 118. Clamping arrangement 104 is movable relative to base 102 between: a first positioning (i.e., open position, e.g., see FIGS. 2-6) in which first clamping surface 116 is spaced from first support surface 112 and second clamping surface 118 is spaced from second support surface 114, and a different second positioning (i.e., closed position, e.g., see FIGS. 7 and 8) in which first clamping surface 116 is engaged, directly or indirectly (i.e., via adhesive arrangement 16 such as shown in FIGS. 7 and 8) with first support surface 112 and second clamping surface 118 is engaged, directly or indirectly (i.e., via adhesive arrangement 16 such a s shown in FIGS. 7 and 8) with second support surface 114. In example embodiments of the present invention, magnets and/or other suitable latching and/or locking mechanisms have been employed to maintain clamping arrangement 104 in the aforementioned second positioning.

From the foregoing it is thus to be appreciated that when clamping arrangement 104 is disposed in the aforementioned first positioning, adhesive arrangement 16 may be placed on base 102 with apertures 40 thereof positioned such that alignment elements 110 extend therethrough, and thus release material 37 disposed on adhesive material 36 is engaged with contoured surface 108 of base 102. Once adhesive arrangement 16 is positioned accordingly, clamping arrangement 104 is moved to such second positioning and adhesive arrangement 16 is secured by clamping arrangement 104 to base 102 in an aligned position therewith, such as shown in FIG. 7. After adhesive arrangement 16 has been secured to base 102, secondary adhesive arrangement 38 is placed on adhesive arrangement 16 with apertures 42 thereof positioned such that alignment elements 110 extend therethrough, and thus a first adhesive surface 38A of secondary adhesive arrangement 38 is directly engaged with and adhered to second planar surface 30 of adhesive arrangement 16. Finally, patient interface 14 is placed on secondary adhesive arrangement 38 with nasal apertures 22 thereof positioned such that alignment elements 110 extend therethrough, and thus countered surface 24 of patient interface 14 is directly engaged with and adhered to a second adhesive surface 38B (opposite first adhesive surface 38A) of secondary adhesive arrangement 38. After all of the aforementioned components are aligned and adhered together, clamping arrangement 104 is returned to the first positioning and the assembly of patient interface 14 and adhesive arrangement 16 is removed from system 100 for use by a patient.

Figure 2:
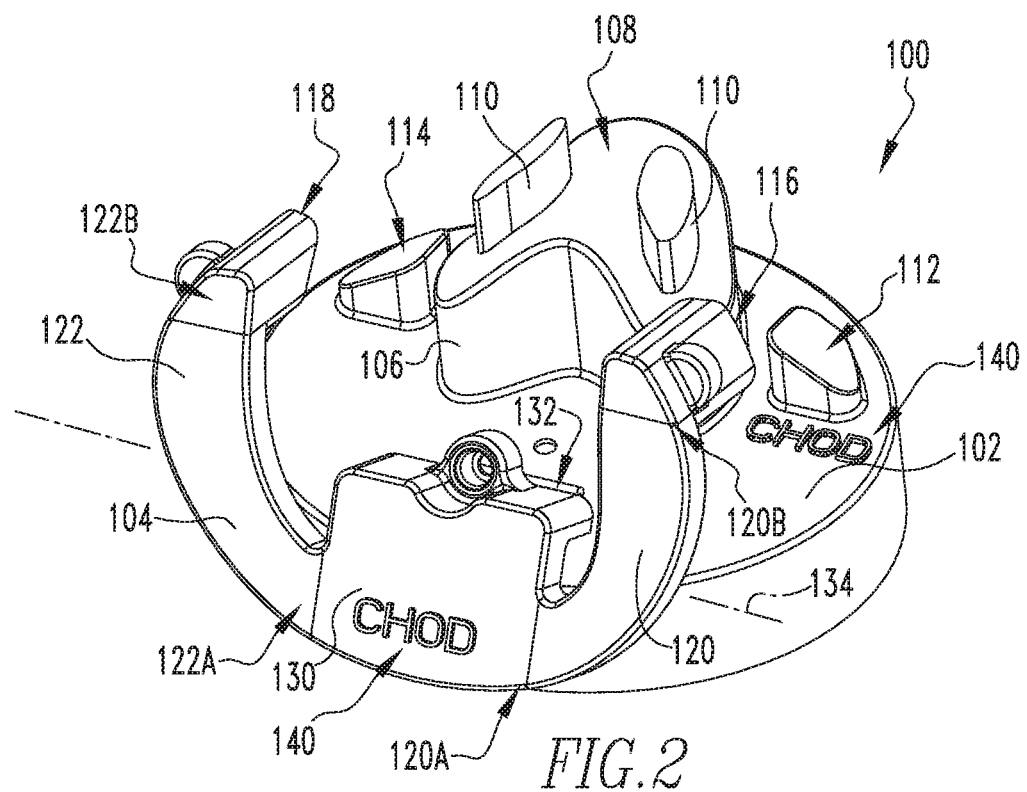
FIG. 2 is a perspective rear view of a system for use in aligning a patient interface and an adhesive arrangement for securing the patient interface to the face of a patient in accordance with one non-limiting example embodiment of the present invention shown with a clamping member of the system disposed in an unclamped positioning.
Figure 3:
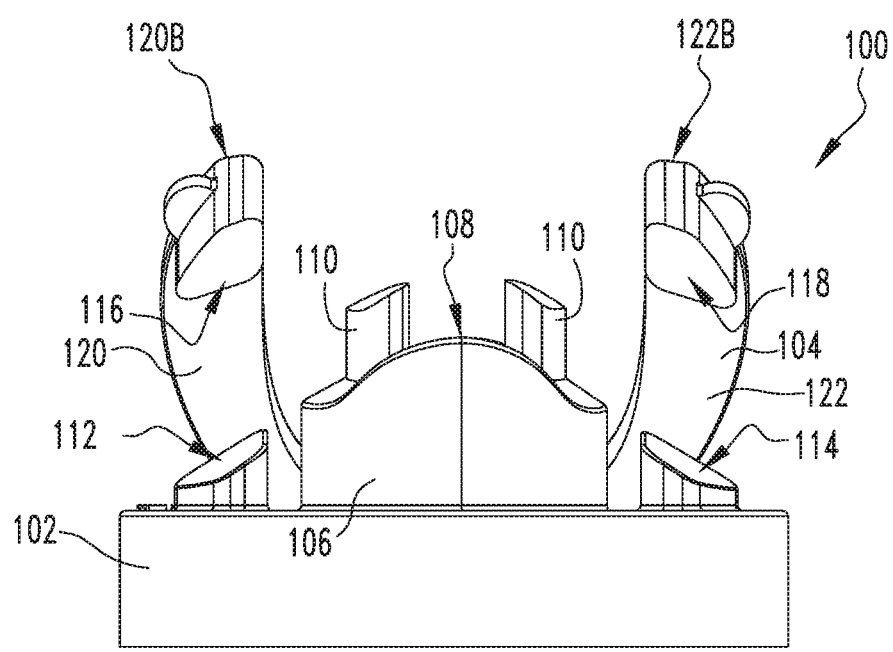
FIG. 3 is a front elevation view of the system of FIG. 2.
Figure 4:
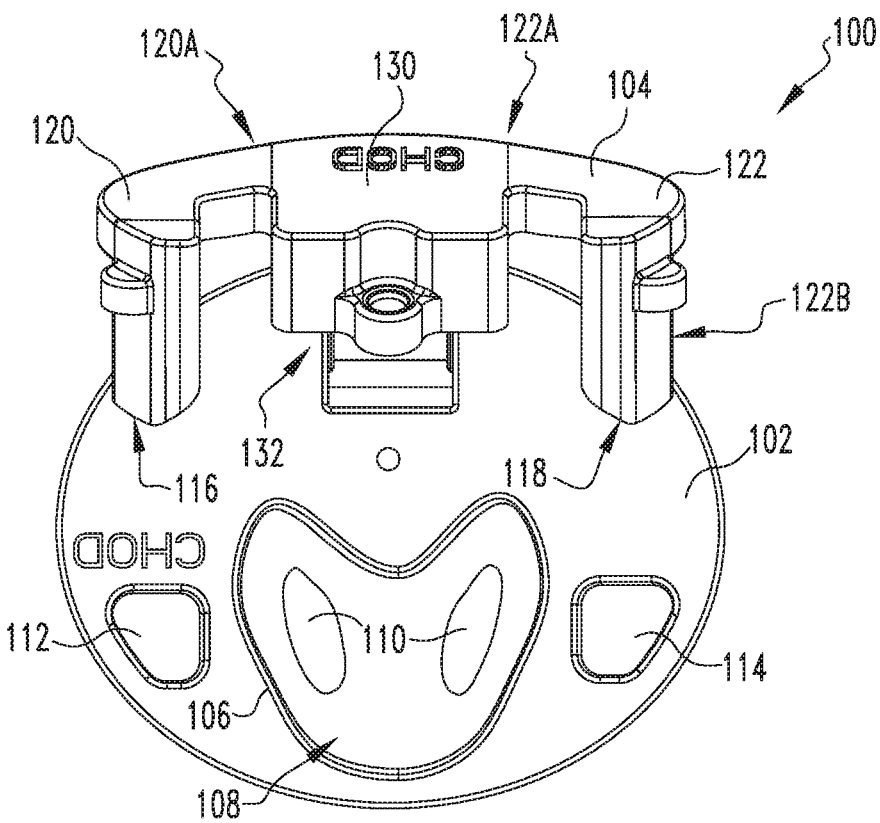
FIG. 4 is a top view of the system of FIG. 2.
Figure 5:
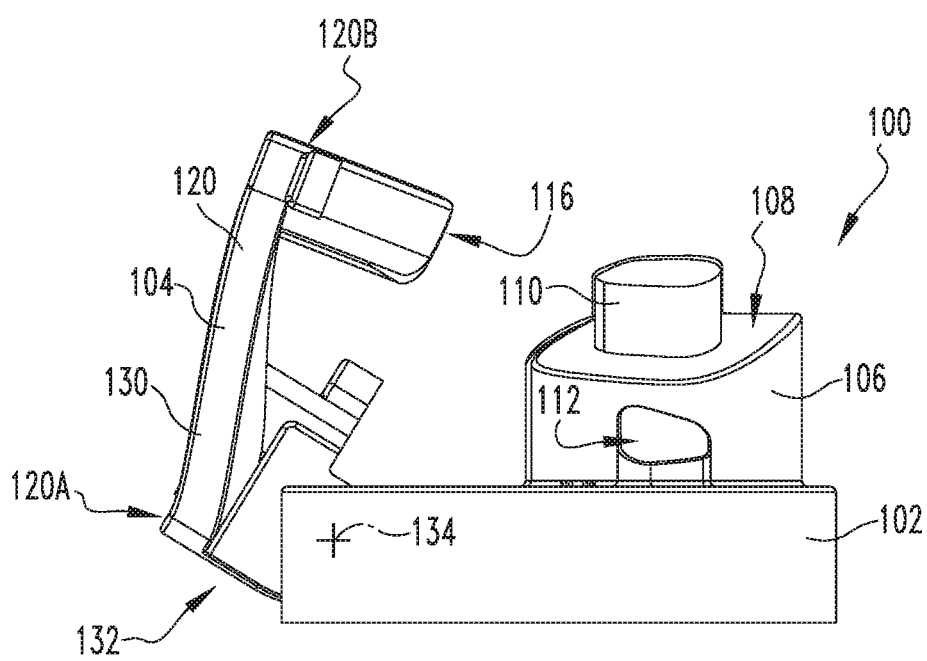
FIG. 5 is a right side elevation view of the system of FIG. 2.
Figure 6:
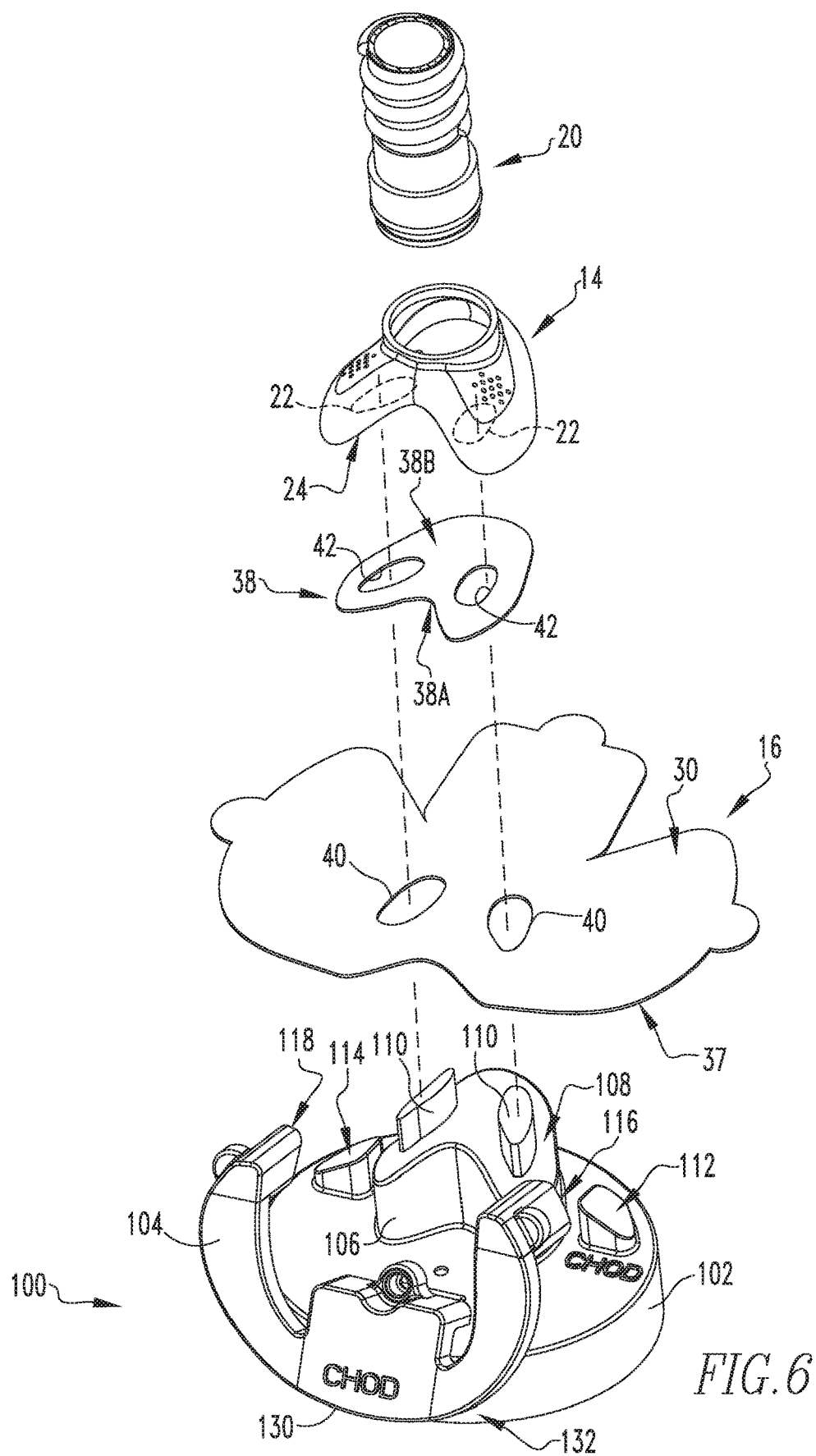
FIG. 6 is another perspective view of the system of FIG. 2 shown with the adhesive arrangement and patient interface of FIG. 1 exploded above prior to alignment.

In the example shown in FIGS. 2-5, clamping arrangement 104 includes: a first arm member 120 having a first end 120A and an opposite second end 120B, and a second arm member 122 having a first end 122A and an opposite second end 122B. First end 120A is moveably coupled to base 102 and first end 122A of second arm member 122 is moveably coupled to base 102. First clamping surface 116 is disposed at or about second end 120B of first arm member 120A and second clamping surface 118 is disposed at or about second end 122B of second arm member 122. In the example of FIGS. 2-5, first arm member 120 and second arm member 122 are each formed as portions of a single unitary member 130 which is coupled to base 102 via a hinge-like arrangement 132 such that unitary member 130 may pivot about a pivot axis 134 (FIGS. 2 and 5). Hence, it may be said that clamping arrangement 104 is pivotally coupled to base 102.

In one example embodiment in accordance with the present invention base 102 was formed as a product of an additive manufacturing process (e.g., 3D printing) using dimensions obtained (e.g., via facial scan, direct measurement, etc.) from the patient for which patient interface 114 was intended. In such embodiment, contoured surface 108 was dimensioned/shaped based on facial dimensions of the patient. Furthermore, first support surface 112, second support surface 114, first clamping surface 116, and second clamping surface 118 were also positioned and shaped based on facial dimensions of the patient. As shown in the example of FIG. 2, custom indicia 140 may be provided on either or both of base 102 and/or clamping arrangement 104 as an integral portion thereof. Custom indicia 140 may be in the form of a name or other identifier for the patient, a custom design or graphic, or other graphical element assigned to, or selected by the patient.

From the foregoing, it is thus to be appreciated that the disclosed concept provides for a system for aligning one or more adhesive components used in securing a patient interface to the face of a patient with an interface device intended for use by the patient in receiving a flow of a breathing gas.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for aligning a patient interface for use in delivering a flow of a breathing gas to the airway of a patient with an adhesive arrangement structured to secure the patient interface to the patient, the system comprising a base structured to be disposed on a surface, the base comprising a central member protruding upward from the base to a contoured surface, the central member including a pair of protruding alignment elements extending further upward from the contoured surface, wherein the patient interface is a nasal mask having a pair of nasal apertures, and wherein each protruding alignment element is sized and configured to cooperatively engage a corresponding nasal aperture of the patient interface device.

2. The system of claim 1, wherein the pair of nasal apertures are defined within a contoured surface of the patient interface, and wherein the contoured surface of the base is of a shape which is structured to coincide with the contoured surface of the patient interface.

3. The system of claim 1, wherein the base is formed from an additive manufacturing process.

4. The system of claim 3 wherein the base is dimensioned, at least in-part, based on dimensions obtained from the patient.

5. The system of claim 4, wherein the contoured surface is dimensioned based on facial dimensions of the patient.

6. The system of claim 1, wherein the base further comprises a custom indicia selected by the patient integrally formed therewith.

7. A system for aligning a patient interface for use in delivering a flow of a breathing gas to the airway of a patient with an adhesive arrangement structured to secure the patient interface to the patient, the system comprising a base structured to be disposed on a surface, the base comprising a central member protruding upward from the base to a contoured surface, the central member including a pair of protruding alignment elements extending further upward from the contoured surface, wherein the system further comprises a clamping arrangement moveably coupled to the base, the clamping arrangement being structured to hold the adhesive arrangement in a predetermined position on the base.

8. The system of claim 7, wherein the base comprises a first support surface structured to support a portion of the adhesive arrangement and a second support surface structured to support another portion of the adhesive arrangement; and wherein the clamping arrangement comprises:
 a first clamping surface; and
 a second clamping surface,
 wherein the clamping arrangement is movable relative to the base between:
  a first positioning in which the first clamping surface is disengaged and spaced from the first support surface and the second clamping surface is disengaged and spaced from the second support surface, and
  a different second positioning in which the first clamping surface is engaged, directly or indirectly with the first support surface and the second clamping surface is engaged, directly or indirectly with the second support surface.

9. The system of claim 8, wherein the clamping arrangement comprises a first arm member having a first end and an opposite second end and a second arm member having a first end and an opposite second end; wherein the first end of the first arm member is moveably coupled to the base; wherein the first end of the second arm member is moveably coupled to the base; wherein the first clamping surface is disposed at or about the second end of the first arm member; and wherein the second clamping surface is disposed at or about the second end of the second arm member.

10. The system of claim 9, wherein the first arm member comprises a first portion of a unitary member moveably coupled to the base and wherein the second arm member comprises a second portion of the unitary member.

11. The system of claim 10, wherein the unitary member is pivotally coupled to the base.

12. The system of claim 8, wherein the first support surface, the second support surface, the first clamping surface, and the second clamping surface are positioned and shaped based on facial dimensions of the patient.

13. A method of aligning a patient interface for use in delivering a flow of a breathing gas to the airway of a patient with a primary adhesive arrangement structured to secure the patient interface to the patient using a system, the system comprising: base structured to be disposed on a surface, the base comprising a central member protruding upward from the base to a contoured surface, the central member including a pair of protruding alignment elements extending further upward from the contoured surface, the method comprising:
 positioning the primary adhesive arrangement on the base such that a pair of first apertures of the primary adhesive arrangement are positioned such that the pair of protruding alignment elements of the base extend through the pair of first apertures;
 positioning a secondary adhesive arrangement on the primary adhesive arrangement such that a pair of second apertures of the secondary adhesive arrangement are positioned such that the pair of protruding alignment elements of the base extend through the pair of second apertures; and
 positioning the patient interface on the secondary adhesive arrangement such that a pair of nasal apertures of the patient interface are positioned such that the pair of protruding alignment elements of the base extend through the pair of nasal apertures.

14. The method of claim 13, wherein the base further comprises a clamping arrangement moveably coupled to the base, the clamping arrangement being structured to hold the primary adhesive arrangement in a predetermined position on the base; and wherein the method further comprises securing the primary adhesive arrangement to the base with the clamping arrangement prior to positioning the secondary adhesive arrangement on the primary adhesive arrangement.

\* \* \* \* \*